US009737550B2

(12) United States Patent
Wandzel

(10) Patent No.: US 9,737,550 B2
(45) Date of Patent: *Aug. 22, 2017

(54) TREATMENT OF CONGESTION USING STEROIDS AND ADRENERGICS

(71) Applicant: Richard A. Wandzel, Orchard Lake, MI (US)

(72) Inventor: Richard A. Wandzel, Orchard Lake, MI (US)

(*) Notice: Subject to any disclaimer, the term of this patent is extended or adjusted under 35 U.S.C. 154(b) by 389 days.

This patent is subject to a terminal disclaimer.

(21) Appl. No.: 14/053,389

(22) Filed: Oct. 14, 2013

(65) Prior Publication Data

US 2014/0107083 A1   Apr. 17, 2014

Related U.S. Application Data

(60) Continuation of application No. 13/042,022, filed on Mar. 7, 2011, now Pat. No. 8,575,140, which is a division of application No. 11/120,100, filed on May 2, 2005, now Pat. No. 7,902,177.

(51) Int. Cl.
| | |
|---|---|
| *A61K 31/573* | (2006.01) |
| *A61K 31/56* | (2006.01) |
| *A61K 45/06* | (2006.01) |
| *A61K 31/4174* | (2006.01) |
| *A61K 31/58* | (2006.01) |
| *A61K 31/137* | (2006.01) |

(52) U.S. Cl.
CPC ............ *A61K 31/58* (2013.01); *A61K 31/137* (2013.01); *A61K 31/4174* (2013.01); *A61K 31/56* (2013.01); *A61K 31/573* (2013.01); *A61K 45/06* (2013.01)

(58) Field of Classification Search
CPC ...... A61K 31/573; A61K 31/56; A61K 45/06; A61K 31/4174
See application file for complete search history.

(56) References Cited

U.S. PATENT DOCUMENTS

| | | | | |
|---|---|---|---|---|
| 4,466,973 A | * | 8/1984 | Rennie | A61K 31/245 514/330 |
| 4,940,728 A | | 7/1990 | Postley | |
| 5,492,689 A | | 2/1996 | Gwaltney, Jr. | |
| 5,830,490 A | | 11/1998 | Weinstein et al. | |
| 6,410,583 B1 | | 6/2002 | Labelle et al. | |
| 6,641,799 B2 | | 11/2003 | Goldberg | |
| 6,843,372 B2 | | 1/2005 | Weinstein | |
| 7,867,508 B1 | | 1/2011 | Smith | |
| 7,902,177 B2 | | 3/2011 | Wandzel | |
| 8,575,140 B2 | | 11/2013 | Wandzel | |
| 2002/0061281 A1 | | 5/2002 | Osbakken et al. | |
| 2004/0053902 A1 | | 3/2004 | Smith | |
| 2004/0235807 A1 | | 11/2004 | Weinrich et al. | |
| 2006/0030550 A1 | | 2/2006 | Lithgow et al. | |

FOREIGN PATENT DOCUMENTS

| | | |
|---|---|---|
| DE | 19924525 A1 | 11/2000 |
| GB | 1192853 A | 5/1970 |

OTHER PUBLICATIONS

Ferguson, A study of the effect of nasal steroid sprays in perennial allergic rhinitis patients with rhinitis medicamentosa, Otolaryngology—Head and Neck Surgery, vol. 125, Issue 3, (Sep. 2001) pp. 253-260.
Physician's Desk Reference 57th Edition, Advair Diskus (2003) p. 1433-1439.
Physician's Desk Reference 57th Edition, Beconase AQ Nasal Spray (2003) p. 1481-1482.
Physician's Desk Reference 57th Edition, Beconase Inhalation Aerosol (2003) p. 1480-1481.
Physician's Desk Reference 57th Edition, Flonase Nasal Spray (2003) p. 1521-1523.
Physician's Desk Reference 57th Edition, Flovent Diskus (2003) p. 1526-1529.
Physician's Desk Reference 57th Edition, Flovent Inhalation Aerosol (2003) p. 1523-1526.
Physician's Desk Reference 57th Edition, Nasacort AQ Nasal Spray (2003) p. 746-747.
Physician's Desk Reference 57th Edition, Nasacort Nasal Inhaler (2003) p. 744-746.
Physician's Desk Reference 57th Edition, Nasarel Nasal Solution 0.025% (2003) p. 1764-1766.
Physician's Desk Reference 57th Edition, Nasonex Nasal Spray (2003) p. 3052-3055.
Physician's Desk Reference 57th Edition, Pulmicort Turbuhaler Inhalation Powder (2003) p. 636-640.
Physician's Desk Reference 57th Edition, Rhinocort Aqua Nasal Spray (2003) p. 640-642.
Physician's Desk Reference 57th Edition, Vancenase AQ Nasal Spray 0.084% (2003) p. 3085-3087.
Physician's Desk Reference 57th Edition, Vancenase PocketHaler Nasal Inhaler (2003) p. 3083-3085.

* cited by examiner

*Primary Examiner* — Sahar Javanmard
(74) *Attorney, Agent, or Firm* — Harness, Dickey & Pierce, P.L.C.

(57) ABSTRACT

A decongestant composition is provided comprising: (a) a safe and effective amount of an adrenergic compound; (b) a safe and effective amount of a steroid; and (c) a pharmaceutically-acceptable carrier. Methods of treating congestion in a human or animal subject are also provided comprising administering to the subject a composition comprising: (a) an adrenergic compound; and (b) a steroid; where the daily dose of the adrenergic compound administered to the subject is from about 1 µg to about 800 µg, and the daily dose of the steroid administered to the subject is from about 1 µg to about 400 µg.

21 Claims, No Drawings

TREATMENT OF CONGESTION USING STEROIDS AND ADRENERGICS

CROSS-REFERENCE TO RELATED APPLICATIONS

This application is a continuation of U.S. patent application Ser. No. 13/042,022, filed on Mar. 7, 2011, now issued U.S. Pat. No. 8,575,140, which is a divisional of U.S. patent application Ser. No. 11/120,100, filed on May 2, 2005, now issued U.S. Pat. No. 7,902,177. The entire disclosures of the above applications are incorporated herein by reference.

The present invention relates to decongestant compositions and methods of treating congestion.

The nose is a specialized structure that serves as the organ for the sense of smell and as an entry to the respiratory tract. The nose filters out foreign materials using specialized tissue known as the nasal mucosa. The nasal mucosa is composed of several cell layers and cell types including mucous cells. Mucous cells secrete mucus to lubricate the walls of the nose, sinuses, and throat and to trap airborne particles (e.g., dust, bacteria, and viruses) that enter the nasal passages. Mucus regularly clears from the nasal passage and sinuses to protect against bacteria and viruses entering the nose and mouth.

If either the nose or the sinuses are obstructed, commonly called a "stuffy nose", it is difficult to breathe, normal drainage does not occur, and infection may result. "Congestion" is commonly used to describe the complex series of events that hinders the ability to breathe through the nose when one has a cold, sinusitis, or an allergic reaction. For example, congestion can include: 1) a physiological response to an irritant that involves increased blood flow to tissues lining the nose, where the increased blood flow causes these tissues to swell thereby physically blocking the nasal passages; 2) fluid buildup such as drainage from an injury to the nose, 3) mucus buildup 4) single nostril blockage resulting from lying on one's side thereby causing receptor cells in the nose to close off one nasal airway, or 5) changes in temperature and/or humidity.

Clinically, congestion is a common part of acute upper respiratory infections (common colds), acute or chronic allergy flare-ups of the nose, and/or acute or chronic non-allergic rhinosinusitis. These disorders are similarly characterized by intense inflammation of the nasal mucosa. Congestion intensifies these disorders making the patient more aware of the related ear fullness, headache, sore throat, muscle and joint aches, fatigue, and cough for example.

Current treatments of nasal congestion include antihistamines, decongestants, steroids, saline, and herbal remedies. Antihistamines block the binding of the histamine mediator cells to histamine receptors of the nasal mucosa and preempt the swelling of nasal membranes, sneezing, and increased nasal secretions associated with histamine release. Decongestants act to constrict blood vessels in the nasal mucosa and thereby decrease tissue swelling and nasal congestion. Steroids similarly reduce inflammation of swollen nasal mucosa. Treatments such as saline and herbal remedies merely add moisture and increase comfort but without actually relieving the congestion.

Administration of these treatments to the nasal mucosa requires delivery of a precise dosage and adherence to a strict regimen as prescribed by a physician or as detailed by the packaging instructions of an over the counter medicine. Often, patients may not follow the instructions and presume that taking a larger than directed dose ("over-medication" or "over-dosage") will provide a speedy recovery. While the over-medication may temporarily improve the congestion, side effects of over-medication or prolonged use include addiction to the decongestant compositions, significant "rebounding" (swelling-relaxing-swelling patterns known as Rhinitis medicamentosa), and may lead to burning, itching, and drying of the nasal passage.

It is desirable to provide a decongestant which alleviates congestion and reduces the amount of drug or active compound delivered to the patient.

SUMMARY OF THE INVENTION

Various embodiments of the present invention provide decongestant compositions comprising a safe and effective amount of an adrenergic compound; a safe and effective amount of a steroid; and a pharmaceutically-acceptable carrier. Other compositions according to the present invention provide decongestant composition unit dosages (e.g., metered nasal spray compositions) comprising an adrenergic compound; a steroid; and a pharmaceutically-acceptable carrier suitable for topical nasal administration. In various embodiments, one of the adrenergic compound and steroid is present at a sub-efficacious level in the unit dosage composition.

Methods for treating nasal congestion in a human or other animal subject are also provided, comprising administering to the subject a composition comprising an adrenergic compound and a steroid, where the daily dose of the adrenergic compound administered to the subject is from about 1 µg to about 800 µg, and the daily dose of the steroid administered to the subject is from about 1 µg to about 400 µg.

It has been found that the compositions and methods of this invention are effective to decrease congestion and enhance respiratory function. Use of these methods and compositions afford advantages versus decongestant compositions and methods among those known in the art, including one or more of enhanced efficacy, reduction of undesired side effects, utility with subjects having cardiovascular disorders, reduction of amount of medicine required, reduced cost of therapy, and dosing flexibility. Further uses, benefits and embodiments of the present invention are apparent from the description set forth herein.

DESCRIPTION

The following description of the preferred embodiment(s) is merely exemplary in nature and is in no way intended to limit the invention, its application, or uses.

The following definitions and non-limiting guidelines must be considered in reviewing the description of this invention set forth herein. The headings (such as "Introduction" and "Summary") and sub-headings used herein are intended only for general organization of topics within the disclosure of the invention, and are not intended to limit the disclosure of the invention or any aspect thereof. In particular, subject matter disclosed in the "Introduction" may include aspects of technology within the scope of the invention and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being a "system" or "carrier") is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As referred to herein, all compositional percentages are by weight of the total composition, unless otherwise specified.

"A" and "an" as used herein indicate "at least one" of the item is present.

As used herein, the term "about," when applied to the value for a parameter of a composition or method of this invention, indicates that the calculation or the measurement of the value allows some slight imprecision without having a substantial effect on the chemical or physical attributes of the composition or method.

The present invention encompasses certain novel compositions and methods for the administration of decongestant compositions to human or other animal subjects. Specific compounds and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

Compositions

Decongestant System

In various embodiments, the present invention provides decongestant compositions comprising a safe and effective amount of an adrenergic compound, a safe and effective amount of a steroid, and a pharmaceutically acceptable carrier. The combination of the adrenergic compound and the steroid is useful against congestion. As used herein, "congestion" is a series of physiological responses that results in the membranes lining the nose becoming swollen due to inflamed blood vessels. Congestion may be caused by colds, allergies, sinus infections, the flu, over-medication, positioning of the body, and other reasons. Compositions and methods of various embodiments reduce nasal mucosa swelling thereby alleviating congestion. Without limiting the mechanism, function or utility of present invention, it is believed that the compositions, in various embodiments, decrease the amount of medicine required to achieve decongestion. This reduced medication amount serves to: 1) diminish side effects common with standard dosage or an over dosage, 2) prevent the "rebound" effect, 3) allow personalized dosage combinations depending on a subject's prior medication routines and/or particular sensitivities, and 4) treat congestion in patients having other disorders, such as hypertension, arrhythmias, or other cardiovascular disorders, who would otherwise be restricted from using compositions containing adrenergic compounds. As detailed later herein, if desired, the combinations and therapies may be individualized to allow for extended treatment times without significant adverse side effects such as the occurrence of rebound congestion after cessation of the therapy.

Adrenergic Compounds

Adrenergic compounds useful herein include compounds which directly or indirectly agonize or antagonize an alpha- or beta-receptor, eliciting a sympathomimetic response. Of particular interest is the peripheral excitatory action of adrenergic compounds on certain types of smooth muscle, such as those in blood vessels supplying skin and mucous membranes, and on gland cells, such as those in salivary and sweat glands. The adrenergic compounds excite the smooth muscle of the blood vessels in the nasal mucosa and cause vasoconstriction, thereby reducing inflammation or congestion. These peripheral excitatory characteristics make adrenergic compounds suitable for treating nasal congestion by reducing inflamed blood vessels in the nasal mucosa.

Many adrenergic compounds are known in the art, including those described in Goodman and Gillman's, *The Pharmacological Basis of Therapeutics*, 9$^{th}$ Edition (1996). Adrenergic compounds useful herein include those selected from the group consisting of albuterol, amantadine, amphetamine, benzephetamine, bitolterol, clonidine, colterol, dextroamphetamine, diethylpropion, dobutamine, dopamine, ephedrine, epinephrine, ethylnorepinephrine, fenfluramine, fenoterol, guanabenz, guanfacine, hydroxyamphetamine, isoetharine, isoproterenol, levodopa, mephenxermine, metaproterenol, metaraninol, methamphetamine, methoxamine, methyldopa, methylphendate, norepinephrine, oxymetazoline, pemoline, phendimetrazine, phenmetrazine, phentermine, phenylephrine, phenylethylamine, phenylpropanolamine, pirbuterol, prenalterol, propylhexedrine, pseudoephedrine, ritodrine, terbutaline, theophylline, tyramine, and derivatives thereof, pharmaceutically acceptable salts and esters thereof, and mixtures thereof. Preferred adrenergic compounds include oxymetazoline, ephedrine, epinephrine, phenylephrine, phenylpropanolamine, pseudoephrine, and mixtures thereof. A particularly preferred adrenergic compound is oxymetazoline.

Steroid

Steroids useful herein include anti-inflammatory steroids, preferably corticosteroids. Corticosteroids are know to effect multiple cell types (mast cells, eosinophils, neutrophils, macrophages, and lymphocytes) and mediators (histamines, eicosanoids, leukotrienes, and cytokines) involved in inflammation. In the nasal passage, steroids effect cells and mediators of the nasal mucosa which cause congestion.

Preferred steroids include beclomethasone, fluticasone, budesonide, mometasone, triamcinolone, dexamethasone, flunisolide, prednisone, and hydrocortisone. Highly preferred steroids are beclomethasone, fluticasone, and mometasone. For example, in embodiments where beclomethasone, fluticasone, or mometasone are used, oxymetazoline may be advantageously incorporated into the composition to provide an effective decongestant.

Pharmaceutically Compositions

Compositions of embodiments of the present invention are preferably provided in unit dosage form. As used herein, a "unit dosage form" is a composition of this invention containing an amount of an adrenergic compound and a steroid that is suitable for administration to a human or lower animal subject, in a single dose, according to good medical practice.

Compositions useful in the methods of this invention comprise a safe and effective amount of an adrenergic compound and a safe and effective amount of a steroid. A "safe and effective" amount of either the adrenergic compound or the steroid is the amount that is sufficient to have the desired therapeutic effect in the human or lower animal subject, without undue adverse side effects (such as toxicity, irritation, or allergic response), commensurate with a reasonable benefit/risk ratio when used in the manner of this invention. The specific safe and effective amount of the adrenergic compound and the steroid will, obviously, vary with such factors as the severity of the congestion being treated, the physical condition of the patient, the nature of concurrent therapy (if any), the specific adrenergic compound and/or steroid used, the specific route of administration and dosage form, the carrier employed, and the desired dosage regimen.

The adrenergic compound is present in compositions of the present invention at from about 1 µg to about 800 µg per daily unit dose, preferably from about 2 µg to about 500 µg per unit dose. In various embodiments, the compound is present at a unit dose level of from about 3 µg to about 200 µg, about 5 µg to about 150 µg, about 7 µg to about 100 µg, or about 10 µg to about 50 µg. In one embodiment, oxymetazoline is present at a level of about 20 µg to about 100 µg, or 30 µg to about 50 µg per unit dose. In one embodiment, phenylephrine is present at a level of from about 500 µg per unit dose.

The steroid is present in compositions of the present invention at from about 1 µg to about 400 µg per daily unit dose. Preferably, the steroid is present at from about 3 µg to about 35 µg, from about 5 µg to about 30 µg, from about 7 µg to about 25 µg, or from about 10 µg to about 20 µg per unit dose.

The specific adrenergic compound(s) and steroid(s) and their levels included in the composition may be independently selected and varied. In various embodiments, a single steroid or adrenergic compound is combined with multiple adrenergic compounds or steroids, respectively. In some embodiments, multiple steroids or adrenergic compounds are combined with multiple adrenergic compounds or steroids, respectively. In some preferred embodiments, the adrenergic compound is oxymetazoline. In some preferred embodiments, the steroid is beclomethasone, mometasone, or fluticasone. A preferred combination comprises oxymetazoline with beclomethasone, mometasone, or fluticasone. The amounts may also be varied depending on the relative amount of the other component. For example, in an embodiment comprising 34.5 µg of oxymetazoline, mometasone may comprise 11.4 µg of the composition. In another example, the same amount of the steroid and the adrenergic compound may be used, for example, 27 µg of triamcinolone may be combined with 27 µg of pseudoephrine.

In various embodiments, compositions of this invention comprise a sub-efficacious amount of at least one of the adrenergic compound and the steroid. A "sub-efficacious amount" is an amount which is safe and effective when administered to a human or other animal subject in a composition or method of this invention, but which if administered separately would have a clinically insignificant effect. In various embodiments, a sub-efficacious amount is less than the amount of the adrenergic compound or steroid which is generally recognized as effective in clinical use, as evidenced by labeling by appropriate health regulatory authorities (e.g., the Food and Drug Administration, in the United States.) In various embodiments, the sub-efficacious amount is less than about 90%, optionally less than about 80%, less than about 75%, less than about 50%, or less than about 30% of such generally recognized clinical levels. In various embodiments, sub-efficacious amounts may be less than about 40 µg, less than 30 µg, less than 20 µg, less than 10 µg, or less than 1 µg. The amount of either component or both components may be present at the sub-efficacious level depending on the prior treatments administered to the patient. For example, a patient who was concurrently taking a medication which limits the amount of ephedrine that can be administered, may utilize a composition of the present invention formulated of 31 µg of budesonide, paired with 7.0 µg of ephedrine, a sub-efficacious amount. In another example, both the adrenergic compound and the steroid are administered in sub-efficacious amounts. In embodiments where more than one adrenergic compound and/or steroid are used, the relative dosage amounts are reduced to provide at least one of the components at a sub-efficacious level.

While not intending to be bound by a particular theory, the compositions and methods of this invention may include administration of an adrenergic compound and the steroid at "synergistic" levels. Accordingly, the therapeutic effect of administering of the combination of the adrenergic compound and steroid is greater than the additive effect of administering the adrenergic compound and the steroid individually. Such effects include one or more of increasing the effect of the adrenergic compound or steroid, increasing the duration of the effect of the adrenergic compound or steroid, making adrenergic compounds and steroids effective at dosage levels that would otherwise be ineffective for relieving congestion, and thereby reducing the cost of decongestants.

Dosage Forms and Optional Materials

The compositions of this invention may be in any of a variety of forms, suitable (for example) for topical or oral administration. The compositions may be of a solid or liquid form. Preferably, the composition is a liquid suitable for topical administration to the nasal mucosa. The composition delivers the adrenergic compound and the steroid to the respiratory tissues to which they are applied (e.g., nose, sinuses, throat, and/or lungs) of a human or animal subject, so as to raise the local concentration of the steroid and adrenergic compound in the tissue.

Techniques and compositions for making dosage forms useful in the methods of this invention are described in the following references, all incorporated by reference herein: 7 Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2d Edition (1976); and U.S. Pat. No. 5,646,139, White et al., issued Jul. 8, 1997.

In various embodiments, the compositions of the present invention are provided in a device that facilitates administration of the adrenergic composition in a unit dosage. Devices suitable for administering unit doses include those known in the art. Such devices include nebulizers, aspirators, inhalers, and nasal sprayers.

Nebulizers work by forming aerosols or converting bulk liquid into small droplets suspended in a breathable gas. In particular, the nebulizers for use herein nebulize liquid formulations of the compositions provided herein. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large droplets from the mist by impaction and allows the droplets to return to the reservoir. The fine aerosol droplets thus produced pass into the nasal passage by the inhaling air/oxygen. (See U.S. Pat. No. 6,667,344, Banerjee, et al., issued Dec. 23, 2003; U.S. Pat. No. 6,340,023, Elkins, issued Jan. 22, 2002; U.S. Pat. No. 5,586,561, Hillard, issued Dec. 24, 1996; U.S. Pat. No. 5,355,872, Riggs, et al., issued Oct. 18, 1994; U.S. Pat. No. 5,186,166, Riggs, et al., issued Feb. 16, 1993; and U.S. Pat. No. 4,865,027, Laanel et al., issued Sep. 12, 1989.)

Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. (U.S. Pat. No. 5,544,647, Jewett et al., issued Aug. 13, 1996.)

A dry powder inhaler is a system operable with a source of pressurized air to produce dry powder particles of a pharmaceutical composition that is compacted into a very small volume. For inhalation, the system has a plurality of chambers or blisters each containing a single dose of the pharmaceutical composition and a select element for releasing a single dose (See, U.S. Pat. No. 6,642,275, Alfonso, et al. issued Nov. 4, 2003; U.S. Pat. No. 6,626,173, Genova, et al., issued Sep. 30, 2003; U.S. Pat. No. 5,694,920, Abrams, et al., issued Dec. 9, 1997; U.S. Pat. No. 5,033,463, Cocozza, issued, Jul. 23, 1991.)

Suitable powder compositions include, by way of illustration, powdered preparations of the active ingredients thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants and co-solvents and may be filled into conventional aerosol containers that are closed by a suitable metering valve.

In preferred embodiments, the composition is in the form of a nasal spray. Preferred nasal sprays are in liquid form such as an aqueous solution or suspension, an oil solution or suspension, or an emulsion, depending on the properties of the composition components. Optional ingredients ensure minimal irritation, proper spray composition, and adequate delivery. Buffers such as citrate, phosphate, and glycine adjust the pH of the nasal spray to prevent irritation to the nose. Moisturizing agents such as propylene glycol and glycerine are also useful in the nasal spray. Other optional ingredients such as polyphosphoesters, polyethylene glycol, high molecular weight polylactic acid, microsphere encapsulations such as polyvinylpyrrolidone, hydroxypropyl cellulose, chitosan, and polystyrene sulfonate enhance the retention time of the composition.

The composition may be administered using nasal sprayers among those known in the art. In one embodiment, the nasal spray is delivered in a non-pressurized dispenser that provides a unit dose of the adrenergic compound and the steroid upon actuating or engaging the dispenser. To prepare the composition, the nasal spray dispenser may be shaken or "primed" (intentional actuation where no composition is administered to the subject) before administration of the composition to the nasal cavity.

In various embodiments, a decongestant nasal spray may comprise a combination of oxymetazoline, beclomethasone, and a liquid pharmaceutically acceptable carrier. The decongestant nasal spray may be operable to deliver a metered unit dose of the oxymetazoline and the beclomethasone. In such an embodiment, each unit dose comprises from about 10 µg to about 100 µg of the oxymetazoline and from about 1 µg to about 80 µg of the beclomethasone. In various embodiments, the unit does comprises from about 15 µg to about 50 µg, preferably from about 20 µg to about 30 µg each of the oxymetazoline and the beclomethasone. Any of the aforementioned steroids, particularly mometasone or fluitcasone, or adrenergic compounds may be substituted for the oxymetazoline and the beclomethasone in the above example.

Methods

The present invention also provides methods for treating nasal congestion in a human or other animal subject, comprising administering the subject a safe and effective amount of an adrenergic compound and a safe and effective amount of a steroid. In various embodiments, such methods are for the treatment of any disorder which is associated with congestion of the upper respiratory system, including colds, flu, and seasonal and other allergies. In some embodiments, methods are provided for the treatment of congestion in a subject which is adrenergic-sensitive. As referred to herein, such "adrenergic-sensitive" subjects are those for whom administration of adrenergics is otherwise contraindicated according to good medical practice, for such reasons as having a hypertension, cardiac arrhythmia, or other cardiovascular disease. In some embodiments, methods are provided for the treatment of congestion in a subject which is steroid-sensitive. As referred to herein, such "steroid-sensitive" subjects are those for whom administration of steroids is otherwise contraindicated as a matter of good medical practice.

In various embodiments, methods comprise administration of a unit dosage form comprising an adrenergic compound and a steroid, preferably where the unit dose of the adrenergic compound administered to the subject is from about 1 µg to about 800 µg, and the unit dose of the steroid administered to the subject is from about 1 µg to about 150 µg. It is understood, however, that the specific ranges and preferred levels of the adrenergic compound and steroid administered as a unit dose, and as a daily dose, will vary according to the specific compounds selected, condition treated, and other factors consistent with sound medical practice.

The composition may be administered once a day or several times a day depending on the particular combination of the steroid and adrenergic compound and the nature and severity of the disorder (e.g., congestion) being treated. In various embodiments, the total daily amount of the decongestant system (adrenergic compound and steroid) administered in various embodiments, may be equivalent to the unit dose. In various embodiments, the total daily amount is a multiple of the unit dose.

In various embodiments, up to 1000 µg, up to 700 µg, up to 500 µg, or up to 300 µg of the decongestant system may be administered. An exemplary total daily amount may include administering six unit doses of 50 µg each using a nasal spray. In such an embodiment, a unit dose may be administered to each nostril three times over a 24 hour period. Another exemplary total daily amount may include administering eight unit doses of 50 µg each using a nasal spray. In such an embodiment, a unit dose may be administered to each nostril four times over a 24 hour period. Any weight combinations of the adrenergic compound and steroid may make the 50 µg. As discussed earlier herein, the amount of the steroid and the adrenergic compound may be modified independently or may be modified based on the amount/type of the other compound. In various embodiments, less than 200 µg of the decongestant system is administered or less than 100 µg is administered.

Variations in the treatment may provide enhanced long term benefits for a subject. For example, a subject who is displaying signs of becoming intolerant to fluticasone for example, may use a composition which substitutes flunisolide for the fluticasone for a period of time and then the patient may return to the use of fluticasone. This allows for a "cycling" of the particular adrenergic compound and/or steroid used such that resistance or intolerance to a particular compound is avoided. Additionally, cycling through various combinations assists the subject and, if present, the attending health care professional in determining which combination(s) maximizes relief using the smallest dosage of the compounds possible and minimizes or prevents any side effects. This is particularly useful for a subject who takes a series of other medications, for example, a patient who takes steroids for arthritis relief. Cycling also includes a two-step or multi-step therapies where the decongestant system is administered for a duration after which time the steroid of the decongestant system, or any suitable steroid disclosed herein, is administered without an adrenergic compound. Alternating between the decongestant system of embodiments of the present invention and the steroid by itself allows for enhanced relief of congestion and maximizes the effectiveness of the decongestant composition.

The present invention is further illustrated through the following non-limiting examples.

Example 1

A metered nasal spray decongestant is prepared to deliver a combination of oxymetazoline and fluticasone. Each spray delivers 50 µg of oxymetazoline and 25 µg of fluticasone. A subject presenting with congestion receives 2 sprays of the decongestant in each nostril, twice a day. A total daily amount of 400 µg of oxymetazoline and 200 µg of fluticasone is administered in a period of 24 hours. The subject receives immediate congestion relief.

Example 2

A metered nasal spray decongestant is prepared to deliver a combination of oxymetazoline and fluticasone. Each spray delivers 25 µg of oxymetazoline and 25 µg of fluticasone. A subject presenting with congestion receives 2 sprays of the decongestant in each nostril, twice a day. A total daily amount of 200 µg of oxymetazoline and 200 µg of fluticasone is administered in a period of 24 hours. The subject receives immediate congestion relief.

The subject of Example 2 uses the decongestant for a period of six weeks. Throughout the six weeks, the subject benefits from immediate relief of the congestion and does not experience the rebound effect.

Example 3

A metered nasal spray decongestant is prepared to deliver a combination of oxymetazoline and fluticasone. Each spray delivers 12.5 µg of oxymetazoline and 25 µg of fluticasone. A subject presenting with congestion receives 2 sprays of the decongestant in each nostril, twice a day. A total daily amount of 100 µg of oxymetazoline and 200 µg of fluticasone is administered in a period of 24 hours. The subject receives immediate congestion relief.

Example 4

A metered nasal spray decongestant is prepared to deliver a combination of oxymetazoline and fluticasone. Each spray delivers 25 µg of oxymetazoline and 12.5 µg of fluticasone. A subject presenting with congestion receives 2 sprays of the decongestant in each nostril, twice a day. A total daily amount of 200 µg of oxymetazoline and 100 µg of fluticasone is administered in a period of 24 hours. The subject receives immediate congestion relief.

Example 5

A metered nasal spray decongestant is prepared to deliver a combination of phenylephrine and fluticasone. Each spray (unit dosage) delivers 250 µg of phenylephrine and 25 µg of fluticasone. A subject presenting with congestion receives 2 sprays of the decongestant in each nostril, twice a day. A total daily amount of 2000 µg of phenylephrine and 200 µg of fluticasone is administered in a period of 24 hours. The subject receives immediate congestion relief.

Example 6

A metered nasal spray according to Example 5 is prepared substituting mometasone for the fluticasone. Substantially similar results are achieved in the subject.

Example 7

A subject with hypertension presents with congestion. A metered nasal spray decongestant comprising oxymetazoline, fluticasone, and mometasone is administered to the subject. The unit dosage of the decongestant includes 25 µg oxymetazoline, 12.5 µg fluticasone, and 12.5 µg mometasone. Congestion is relieved and the subject does not experience increased blood pressure.

The above composition may be varied by substituting another steroid, e.g., budesonide, for mometasone, with substantially similar results.

Example 8

A subject presents with congestion. A metered nasal spray decongestant comprising mometasone, oxymetazoline, and phenylephrine is administered to the subject. The unit dosage of the decongestant includes 20 µg mometasone, 10 µg oxymetazoline, and 10 μg phenylephrine. The subject receives 2 sprays of the decongestant in each nostril, twice a day. A total daily amount of 160 μg mometasone, 80 μg oxymetazoline, and 80 μg of phenylephrine is administered in a period of 24 hours.

The above composition may be varied by substituting another steroid, e.g., triamcinolone, for mometasone, with substantially similar results.

Example 9

A metered nasal spray decongestant is prepared to deliver a combination of oxymetazoline and budesonide. Each spray (unit dosage) delivers 25 μg of oxymetazoline and 32 μg of budesonide. A subject presenting with congestion receives 2 sprays of the decongestant in each nostril, once a day. A total amount of 100 μg of oxymetazoline and 128 μg of budesonide is administered in a period of 24 hours. The subject receives immediate congestion relief.

Example 10

A metered nasal spray decongestant is prepared according to Example 9. A subject presenting with congestion receives 4 sprays of the decongestant in each nostril, once a day. A total amount of 200 μg of oxymetazoline and 256 μg of budesonide is administered in a period of 24 hours. The subject receives immediate congestion relief.

Example 11

A metered nasal spray decongestant is prepared to deliver a combination of oxymetazoline and mometasone. Each spray delivers 25 μg of oxymetazoline and 25 μg of mometasone. A subject presenting with congestion receives 2 sprays of the decongestant in each nostril, twice a day. A total daily amount of 200 μg of oxymetazoline and 200 μg of mometasone is administered in a period of 24 hours. The subject receives immediate congestion relief.

The above composition may be varied by substituting another steroid, e.g., fluticasone, for mometasone, with substantially similar results.

Example 12

A metered nasal spray decongestant is prepared to deliver a combination of oxymetazoline and mometasone. Each spray delivers 25 μg of oxymetazoline and 15 μg of mometasone. A subject presenting with congestion receives 2 sprays of the decongestant in each nostril, twice a day. A total daily amount of 200 μg of oxymetazoline and 120 μg of mometasone is administered in a period of 24 hours. The subject receives immediate congestion relief.

The above composition may be varied by substituting another steroid, e.g., budesonide, for mometasone, with substantially similar results.

Example 13

A metered nasal spray decongestant is prepared to deliver a combination of oxymetazoline and flunisolide. Each spray delivers 25 μg of oxymetazoline and 25 μg of flunisolide. A subject presenting with flu and congestion receives 2 sprays of the decongestant in each nostril, twice a day. A total daily amount of 200 μg of oxymetazoline and 200 μg of flunisolide is administered in a period of 24 hours. The subject receives immediate congestion relief.

Example 14

A metered nasal spray decongestant is prepared to deliver a combination of oxymetazoline and triamcinolone. Each spray delivers 25 μg of oxymetazoline and 55 μg of triamcinolone. A subject presenting with congestion receives 2 sprays of the decongestant in each nostril, twice a day. A total daily amount of 200 μg of oxymetazoline and 220 μg of triamcinolone is administered in a period of 24 hours. The subject receives immediate congestion relief.

Example 15

A metered nasal spray decongestant is prepared to deliver a combination of oxymetazoline and triamcinolone. Each spray delivers 25 μg of oxymetazoline and 27.5 μg of triamcinolone. A subject presenting with congestion receives 2 sprays of the decongestant in each nostril, twice a day. A total daily amount of 200 μg of oxymetazoline and 110 μg of triamcinolone is administered in a period of 24 hours. The subject receives immediate congestion relief.

Example 16

A metered nasal spray decongestant is prepared to deliver a combination of oxymetazoline and mometasone. Each spray delivers 12.5 μg of oxymetazoline and 25 μg of mometasone. A subject presenting with congestion receives 2 sprays of the decongestant in each nostril, twice a day. A total daily amount of 100 μg of oxymetazoline and 200 μg of mometasone is administered in a period of 24 hours. The subject receives immediate congestion relief.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A method for treating nasal decongestion in a human or other animal subject, comprising administering to the subject a nasal spray composition consisting of oxymetazoline, a nasal corticosteroid, and a liquid pharmaceutically-acceptable carrier, in one or more doses, wherein each dose consists of one or more sprays of the composition in one or both nostrils of the subject, the amount of oxymetazoline administered to a nostril in each dose is about 25 μg to about 100 μg, the amount of the nasal corticosteroid administered to a nostril in each dose is about 25 μg to about 130 μg, the daily dosage of the oxymetazoline is from about 50 μg to about 400 μg, the daily dosage of the nasal corticosteroid is from about 50 μg to about 450 μg, and the amounts of the oxymetazoline and of the nasal corticosteroid are synergistic.

2. The method for treating nasal decongestion in a human or other animal subject according to claim 1, wherein the nasal corticosteroid is selected from the group consisting of beclomethasone, budesonide, dexamethasone, flunisolide, fluticasone, hydrocortisone, mometasone prednisone, triamcinolone, and mixtures thereof.

3. The method for treating nasal decongestion in a human or other animal subject according to claim 2, wherein the nasal corticosteroid is mometasone or fluticasone.

4. The method for treating nasal decongestion in a human or other animal subject according to claim 1, comprising administering the nasal spray composition, in a metered unit dosage spray, wherein each unit dosage spray consists of from about 10 µg to about 50 µg of oxymetazoline.

5. The method for treating nasal decongestion in a human or other animal subject according to claim 4, wherein the metered unit dosage spray is administered from 1 to 4 times per day in each nostril of the subject.

6. The method for treating nasal decongestion in a human or other animal subject according to claim 1, wherein the nasal spray composition is administered for a period of time after which a second composition is administered to the subject, wherein the second composition comprises a steroid without an adrenergic compound.

7. A method for treating nasal decongestion in a human or other animal subject, comprising administering to the subject a unit dosage nasal spray composition, each spray consisting essentially of:
(a) oxymetazoline, at a level of from about 10 µg to about 50 µg;
(b) a safe and effective amount of nasal corticosteroid, at a level of from about 10 µg to about 55 µs; and
(c) a pharmaceutically-acceptable carrier suitable for topical nasal administration; wherein the unit dosage spray is administered from 1 to 4 times per day in each nostril of the subject in a dosage regimen consisting of one or two doses per day, each dose consisting of one or two sprays in each nostril of the subject.

8. The method for treating nasal decongestion in a human or other animal subject according to claim 7, wherein the daily dosage of the oxymetazoline is from about 25 µg to about 400 µg.

9. The method for treating nasal decongestion in a human or other animal subject according to claim 7, wherein the unit dosage composition is administered once or twice per day in each nostril of the subject.

10. The method for treating nasal decongestion in a human or other animal subject according to claim 9, wherein the unit dosage composition is administered once per day in each nostril of the subject.

11. The method for treating nasal decongestion in a human or other animal subject according to claim 7, wherein the nasal corticosteroid is selected from the group consisting of beclomethasone, budesonide, dexamethasone, flunisolide, fluticasone, hydrocortisone, mometasone, prednisone, triamcinolone, and mixtures thereof.

12. The method for treating nasal decongestion in a human or other animal subject according to claim 11, wherein the nasal corticosteroid is mometasone.

13. The method for treating nasal decongestion in a human or other animal subject according to claim 11, wherein the nasal corticosteroid is fluticasone.

14. The method for treating nasal decongestion in a human or other animal subject according to claim 5, wherein the metered unit dosage spray is administered in a dosage regimen consisting of two doses per day, each dose consisting of two sprays in each nostril of the subject.

15. A method for treating nasal decongestion in a human or other animal subject, comprising administering to the subject a nasal spray composition consisting of oxymetazoline, a nasal corticosteroid, and a liquid pharmaceutically-acceptable carrier, in one or more doses, wherein each dose consists of one or more sprays of the composition in one or both nostrils of the subject, and the amount of the oxymetazoline administered in each dose is about 25 µg to about 200 µg, the amount of the nasal corticosteroid administered in each dose is about 50 µg to about 260 µg, and the levels of the oxymetazoline and of the nasal corticosteroid are synergistic.

16. The method for treating nasal decongestion in a human or other animal subject according to claim 15, wherein the combined daily dose of the oxymetazoline and the nasal corticosteroid is 700 µg or less.

17. The method for treating nasal decongestion in a human or other animal subject according to claim 16, wherein the combined daily dose of the oxymetazoline and the nasal corticosteroid is 500 µg or less.

18. The method for treating nasal decongestion in a human or other animal subject according to claim 15, wherein the nasal corticosteroid is selected from the group consisting of beclomethasone, budesonide, dexamethasone, flunisolide, fluticasone, hydrocortisone, mometasone prednisone, triamcinolone, and mixtures thereof.

19. The method for treating nasal decongestion in a human or other animal subject according to claim 18, wherein the nasal corticosteroid is mometasone or fluticasone.

20. The method for treating nasal decongestion in a human or other animal subject according to claim 15, comprising administering the nasal spray composition, in a metered unit dosage spray, wherein each unit dosage spray consists of from about 10 µg to about 50 µg of oxymetazoline.

21. The method for treating nasal decongestion in a human or other animal subject according to claim 15, wherein the unit dosage composition is administered once or twice per day in each nostril of the subject.

* * * * *

UNITED STATES PATENT AND TRADEMARK OFFICE
CERTIFICATE OF CORRECTION

PATENT NO. : 9,737,550 B2
APPLICATION NO. : 14/053389
DATED : August 22, 2017
INVENTOR(S) : Richard A. Wandzel Page 1 of 1

It is certified that error appears in the above-identified patent and that said Letters Patent is hereby corrected as shown below:

In the Claims

Column 13, Line 23 (Claim 7):
"µs" should be -- µg --

Signed and Sealed this
Twenty-fourth Day of October, 2017

Joseph Matal
*Performing the Functions and Duties of the
Under Secretary of Commerce for Intellectual Property and
Director of the United States Patent and Trademark Office*